United States Patent
Loupas et al.

(10) Patent No.: US 11,899,142 B2
(45) Date of Patent: Feb. 13, 2024

(54) ULTRASOUND SYSTEM WITH IMPROVED NOISE PERFORMANCE BY PERSISTENCE PROCESSING

(71) Applicant: KONINKLIJKE PHILIPS N.V., Eindhoven (NL)

(72) Inventors: Thanasis Loupas, Kirkland, WA (US); Paul Sheeran, Woodinville, WA (US); Charles Tremblay-Darveau, Seattle, WA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 844 days.

(21) Appl. No.: 16/964,615

(22) PCT Filed: Jan. 15, 2019

(86) PCT No.: PCT/EP2019/050877
§ 371 (c)(1),
(2) Date: Jul. 24, 2020

(87) PCT Pub. No.: WO2019/145188
PCT Pub. Date: Aug. 1, 2019

(65) Prior Publication Data
US 2021/0055398 A1 Feb. 25, 2021

Related U.S. Application Data

(60) Provisional application No. 62/621,187, filed on Jan. 24, 2018.

(51) Int. Cl.
*G01S 7/52* (2006.01)
*A61B 8/06* (2006.01)
*A61B 8/14* (2006.01)
*A61B 8/08* (2006.01)
*G01S 15/89* (2006.01)

(52) U.S. Cl.
CPC ............ *G01S 7/52077* (2013.01); *A61B 8/06* (2013.01); *A61B 8/14* (2013.01); *A61B 8/488* (2013.01); *A61B 8/5246* (2013.01); *A61B 8/5276* (2013.01); *G01S 15/8906* (2013.01)

(58) Field of Classification Search
None
See application file for complete search history.

(56) References Cited

U.S. PATENT DOCUMENTS 5,833,613 A 11/1998 Aerkiou et al.
5,865,752 A 2/1999 Seyed-Bolorforosh et al.
(Continued)

OTHER PUBLICATIONS

PCT/EP2019/050877 ISR & WO, Apr. 8, 2019, 17 Pages.

*Primary Examiner* — Hovhannes Baghdasaryan

(57) ABSTRACT

An ultrasound system produces persisted images in response to both persistence coefficients and noise bias coefficients. The persistence coefficients control the degree of persistence, which reduces noise variance by persistence processing. The noise bias coefficients are produced in correspondence with the likelihood that an image pixel is noise, and operate to reduce the noise floor of the persisted images. A single user control enables a user to control both the noise variance and the noise level of images in tandem or, alternatively, dedicated controls can become available to adjust noise variance and noise level separately.

9 Claims, 5 Drawing Sheets

(56) References Cited

U.S. PATENT DOCUMENTS 6,120,446 A * 9/2000 Ji .................... G01N 29/2456
600/443
6,423,003 B1 7/2002 Ustuner et al.

* cited by examiner

United States Patent

ULTRASOUND SYSTEM WITH IMPROVED NOISE PERFORMANCE BY PERSISTENCE PROCESSING

CROSS-REFERENCE TO PRIOR APPLICATIONS

This application is the U.S. National Phase application under 35 U.S.C. § 371 of International Application No. PCT/EP2019/050877, filed on Jan. 15, 2019, which claims the benefit of U.S. Provisional Patent Application No. 62/621,187, filed on Jan. 24, 2018. These applications are hereby incorporated by reference herein.

This invention relates to ultrasound systems and, in particular, to ultrasonic imaging systems which process images with persistence and reduce image noise.

There are numerous sources of noise that appear in ultrasound images as unwanted image artifacts. One noise source is speckle noise which arises due to the coherent nature of ultrasound imaging. Speckle is caused by the intermodulation of signals from different signal paths in the image field, resulting in a mottled appearance in what should appear as uniformly smooth tissue. Two approaches which are in widespread use for reducing image speckle are frequency compounding as described in U.S. Pat. No. Re. 35,148 (Lizzi et al.) and spatial compounding as described in U.S. Pat. No. 6,126,598 (Entrekin et al.) Another source of image noise is r.f. radiation from nearby electrical equipment. This noise is reduced by shielding ultrasound systems and transducers from radio frequency interference, and by electrical line filtering. Yet another source of noise is out-of-band noise in transducers. This noise is reduced by shaping the passband used to receive and process the desired ultrasound signals. A further source of image noise is that developed in the electrical components and circuitry used in an ultrasound system, such as the amplifiers used to amplify the received signals. These components and circuits have an inherent noise floor, which is desirably reduced to as low a level as possible. These latter sources of noise can be reduced by combining consecutively acquired images. Since much of this noise is random in nature, combining the pixels of consecutive images on a pixel-by-pixel basis will average out some of this noise. One image processing technique which was introduced for another purpose and will reduce noise by image combining is known as persistence processing. A number of biological functions in the body will produce a function to be imaged only momentarily, and often too rapidly to be easily discerned in a diagnosis. One such function is the maximum blood flow velocity in turbulent blood flow at peak systole, which occurs when the blood flow pressure is at its maximum. Persistence was developed to aid in discerning such moments of peak blood flow, and does so by extending or persisting the appearance of such peak blood flow in color Doppler imaging. Several consecutive image frames of blood flow are continually combined so that the peak flow appears in the image for several displayed frames, increasing the likelihood that the clinician will spot the occurrence of the peak flow velocity. Each frame used in the combination has a weighting factor which causes its effect on the combination to diminish after several displayed images. Thus, the blood flow peak will not appear in just one frame, but will persist with diminishing effect for several frames, making it easier to discern in the image sequence. Since the persistence technique performs its image combining on a pixel-by-pixel basis, the process will inherently average out random noise in the combined images as a function of the square root of the number of images which are combined. The speckle artifact will also be reduced by averaging. Unfortunately, because of the incoherent nature of the temporal averaging involved in the persistence processing, this noise reduction only results in a reduction of the variance of noise artifacts; it does not reduce the mean noise level (i.e. "noise floor") itself. Accordingly, it would be desirable to implement a noise reduction technique that has the effect of reducing the noise floor, increasing the signal to noise ratio of the image to produce a more noise-free ultrasound image.

In accordance with the principles of the present invention, an ultrasound system employs a persistence processor which is capable of reducing the noise floor and therefore improve the signal to noise ratio of an ultrasound image. The signal content of each pixel in an ultrasound image is analyzed in relation to a signal versus noise model to determine its likelihood of being either signal or noise. The results of this analysis are used to produce a noise bias coefficient or weighting factor which is applied to each pixel on a pixel-by-pixel basis in the course of persistence processing. The result is an image with a noise floor which is reduced in proportion to the applied persistence. The inventive system produces enhanced noise reduction with less persistence, improving the sensitivity and the temporal clarity of the ultrasound images in the presence of anatomical motion.

FIGS. 3$a$ and 3$b$ illustrate a technique for classifying image pixels in accordance with their likelihood of being noise.

FIGS. 4$a$, 4$b$ and 4$c$ illustrate several conversion curves which may be used to create noise bias coefficients in accordance with the present invention.

Figure 5:
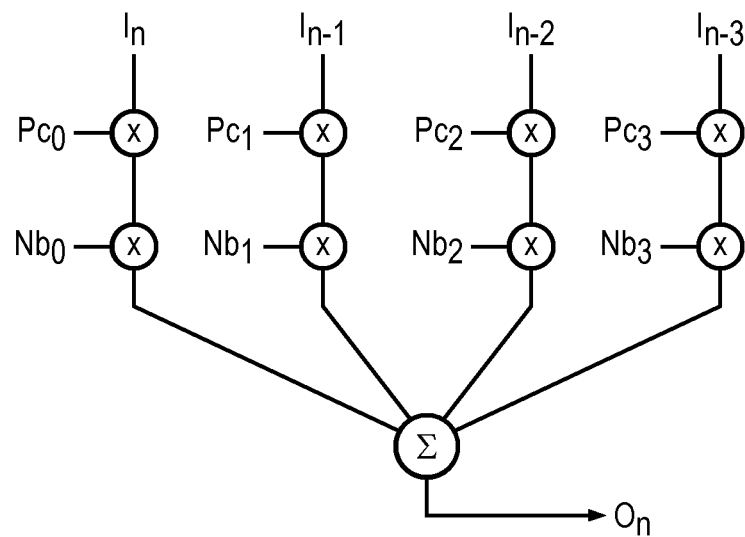

FIG. 5 illustrates a persistence processor of the present invention that is constructed as a finite impulse response (FIR) filter network.

FIGS. 6$a$ and 6$b$ illustrate persistence processors of the present invention constructed as infinite impulse response (IIR) filter networks.

The below references one or more processors and memories associated with the processors, in which the processors execute function in accordance with instructions. It is understood that a processor associated with a particular function as described herein may be the same or different processor from another processor associated with a particular function. For example, one skilled in the art would understand that one processor or a plurality of processors may be inclusive of the processors described herein as an image processor, a noise bias coefficient processor, and a persistence processor, for example.

Figure 1:
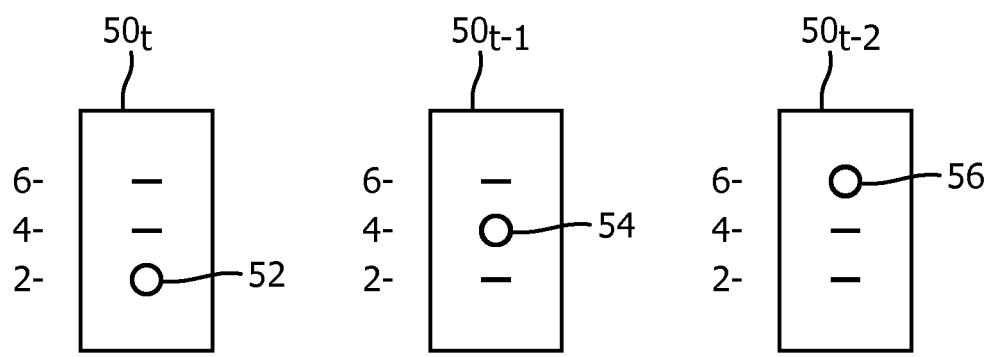
FIG. 1 illustrates how noise is reduced by conventional persistence processing or other image combining techniques.

FIG. 1 illustrates how noise is reduced by persistence processing of images or other image combination techniques. Blocks $50_t$, $50_{t-1}$, and $50_{t-2}$ represent three image pixels or groups of pixels at a common location in three consecutive ultrasound images. In this example the pixels are all noise, with magnitudes shown by the height of circles 52, 54, and 56 in the blocks, and indicated by the numerical scale adjacent each block. The values of noise in the three images are 2, 4, and 6, respectively. The average of the three noise values is four, with a variance of four. If a persistence processor were to combine the pixels of the first two images $50_t$ and $50_{t-1}$, the average of the noise values would be three.

Similarly, if the persistence processor were to combine the pixels of the second and third images $50_{t-1}$ and $50_{t-2}$, the average would be five. Thus, the noise values would span a range of three to five with a variance of two, but their average would still be four. Thus, the variance of the noise values has been reduced from a span of four to a span of two, but the noise level remains at four. A conventional persistence processor reduces the noise variance, but not the noise level of the images.

Figure 2:
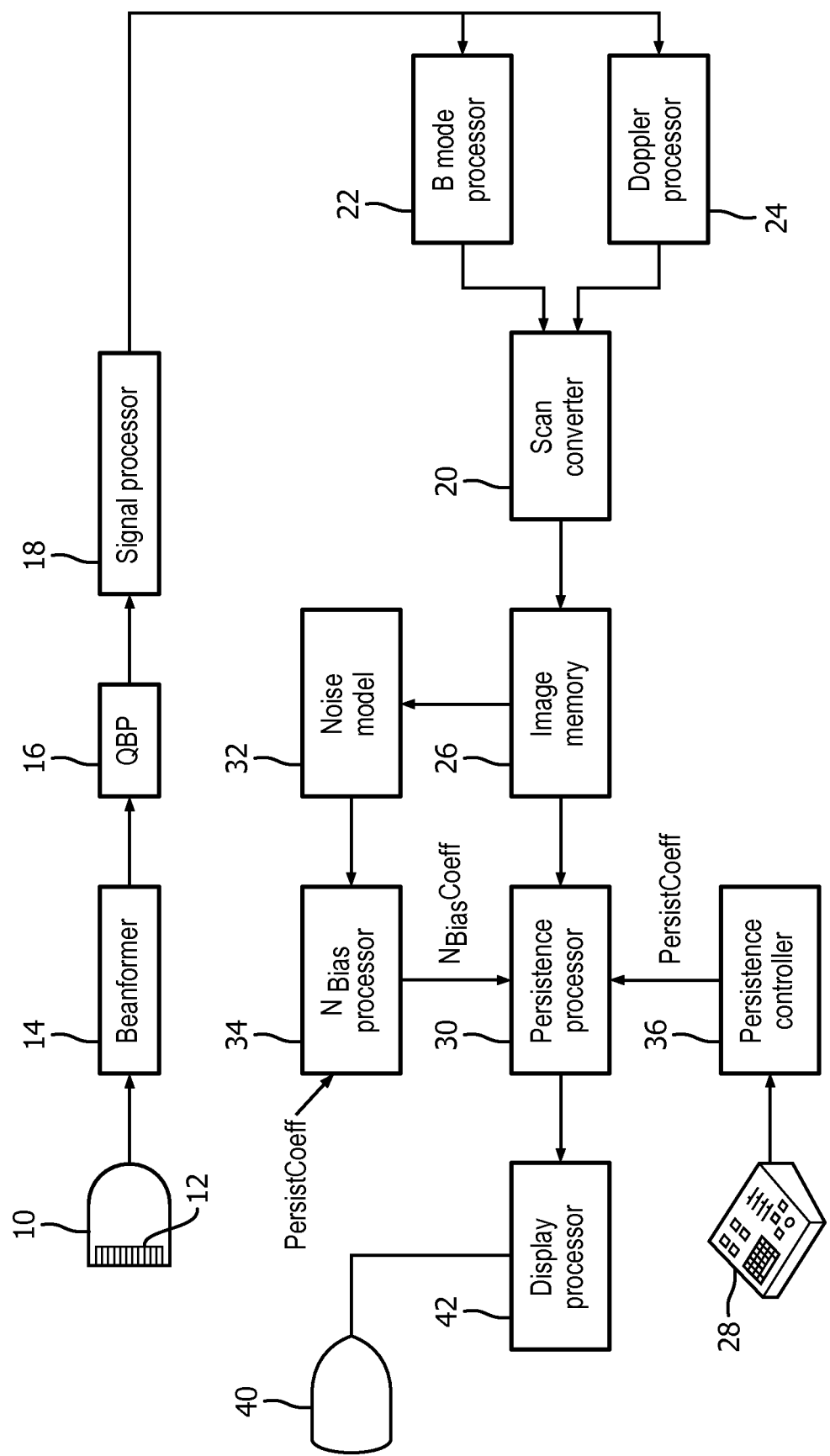
FIG. 2 illustrates in block diagram form an ultrasound system constructed in accordance with the principles of the present invention.

Referring now to FIG. 2, an ultrasonic imaging system constructed in accordance with the principles of the present invention is shown in block diagram form. A transducer array 12 is provided in an ultrasound probe 10 for transmitting ultrasonic waves and receiving ultrasonic echo information. The transducer array 12 may be a one- or two-dimensional array of transducer elements capable of scanning in two or three dimensions, for instance, in both elevation (in 3D) and azimuth. A two-dimensional array probe will include a microbeamformer coupled to the array elements which controls transmission and reception of signals by the array elements. Microbeamformers are capable of at least partial beamforming of the signals received by groups or "patches" of transducer elements as described in U.S. Pat. No. 5,997,479 (Savord et al.), U.S. Pat. No. 6,013,032 (Savord), and U.S. Pat. No. 6,623,432 (Powers et al.) The microbeamformer or the transducer elements are coupled by a probe cable to a beamformer 14. The transmission of ultrasonic beams from the transducer array 12 under control of a microbeamformer when so equipped, or directly if there is no microbeamformer, is directed by a transmitter in the beamformer, which receives input from the user's operation of a user interface or control panel 28 of the ultrasound system. Among the transmit characteristics controlled by the transmitter are the frequency, amplitude, phase, and polarity of transmit waveforms. Beams formed in the direction of pulse transmission may be steered straight ahead from (orthogonal to) the transducer array, or at different angles to scan a wider field of view.

The echoes received by a contiguous group of transducer elements are beamformed in the beamformer 14 by appropriately delaying them and then combining them. Analog beamformers are known, but modern ultrasound systems perform beamforming in the digital domain by converting received echo signals to digital signal samples prior to beamformation. The partially beamformed signals produced by a microbeamformer are digitized and combined into fully beamformed coherent echo signals by the beamformer.

The coherent echo signals are coupled to a quadrature bandpass filter (QBP) 14. The QBP performs three functions: band limiting the RF echo signal data, producing in-phase and quadrature pairs (I and Q) of echo signal data, and decimating the digital sample rate. The QBP comprises two separate filters, one producing in-phase samples and the other producing quadrature samples, with each filter being formed by a plurality of multiplier-accumulators (MACs) implementing an FIR filter. The quadrature signal samples undergo signal processing by a signal processor 18, which includes filtering by a digital filter and speckle reduction as by spatial or frequency compounding. The signal processor can also shift the frequency band to a lower or baseband frequency range, as can the QBP. The signal processor can also discriminate signals in harmonic frequency bands by filtering or pulse inversion. The digital filter of the signal processor 18 can be a filter of the type disclosed in U.S. Pat. No. 5,833,613 (Averkiou et al.), for example.

The beamformed and processed coherent echo signals are coupled to one or more image processors. A B mode processor 22 produces a B mode image of structure in the body such as tissue. The B mode processor performs amplitude (envelope) detection of quadrature demodulated I and Q signal components by calculating the echo signal amplitude in the form of $(I^2+Q^2)^{1/2}$. The B mode processor also applies log compression to B mode image values. The quadrature echo signal components are also coupled to a Doppler processor 24. The Doppler processor stores ensembles of echo signals from discrete points in an image field which are then used to estimate the Doppler shift at points in an image by fast Fourier transform (FFT) processing. The Doppler shift is proportional to motion at points in the image field, e.g., blood flow and tissue motion. For a color Doppler image, the estimated Doppler flow values at each point in a blood vessel are wall filtered and converted to color values using a look-up table. The B mode image signals and the Doppler flow values are coupled to a scan converter 20 which converts the B mode and Doppler samples from their acquired R-θ coordinates to Cartesian (x,y) coordinates for display in a desired display format, e.g., a rectilinear display format or a sector display format. Either the B mode image or the Doppler image may be displayed alone, or the two shown together in anatomical registration in which the color Doppler overlay shows the blood flow locationally in tissue and vessels in the image. A succession of received and processed ultrasound images are stored in an image memory 26.

In accordance with the principles of the present invention, image noise is reduced prior to display by a persistence processor 30. The noise reduction uses a noise model 32 with data representing the noise level of pixels in an image, which may be configured in various ways. One way is to base the noise model on knowledge of the noise power versus gain of the receive amplifiers of the system. The noise power of the system amplifiers as a function of gain is measured at the factory and aggregated in a number of models for different probe apertures and gain levels. The noise models are stored in memory in the ultrasound system and one is accessed during imaging depending on the probe aperture used and the setting of the user gain control. Another way to configure the noise model is by cross correlating consecutively received images from a stationary image field such as a phantom or air. In the absence of noise, commonly located pixels in the two images will perfectly correlate, indicating the absence of noise. A low degree of correlation indicates a strong presence of noise. A table is thus constructed and stored in memory of correlation values representing the degree of noise presence in the image field. The consecutive images which are correlated can be two dimensional or one dimensional (line) images.

Another technique for configuring a noise model is from the reception of an image in the absence of ultrasound signal transmission. Ideally, the received image will exhibit a complete absence of signal, but if any is present it is assumed to be due to noise. A table of the measured levels of pixels in an image, assumed to be due to noise, is stored in memory and used as the noise model. Yet another technique for configuring a noise model is to set the receiver filters to a noise portion of the received signal spectrum, a frequency at which there should be no ultrasonic signal energy. A table of the measured levels of pixels in the image corresponding to the noise-centered receive filters is then stored in memory as the noise model.

Figure 3A:
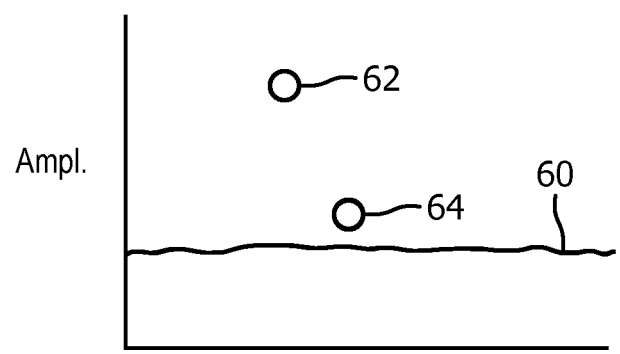

The pixels of an image to be processed in accordance with the present invention are compared to the values of the noise model to assess the likelihood that a pixel is noise. Examples of this comparison are shown in FIG. 3. Reference numeral 60 indicates the noise level for a pixel location of the noise model and 62 and 64 are pixels of images received at that location. Received image pixel 62 in FIG. 3a is seen to be well above the noise floor 60 and thus has a low likelihood of being noise. Its noise likelihood index value may be 10%, for instance. Another received image pixel 64 has an amplitude very close to the noise floor 60, and thus has a high likelihood of being noise. This pixel may be assigned a noise likelihood index (NLI) value of 95%, for example.

Figure 3B:
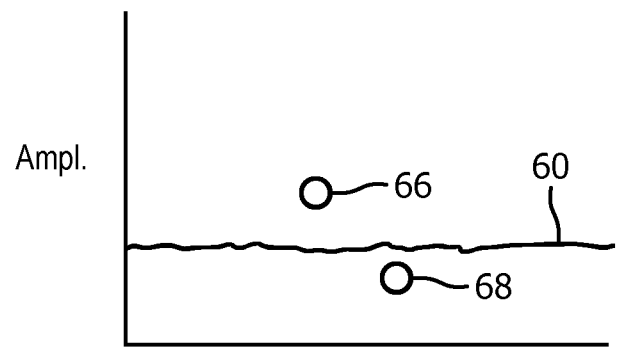

FIG. 3b illustrates two other examples of noise likelihood classification. Pixel 66 is relatively close to the noise floor 60 and may be assigned a NLI value of 25%. Pixel 68 has an amplitude below the noise floor 60, and its NLI value is 100%.

Figure 4A:
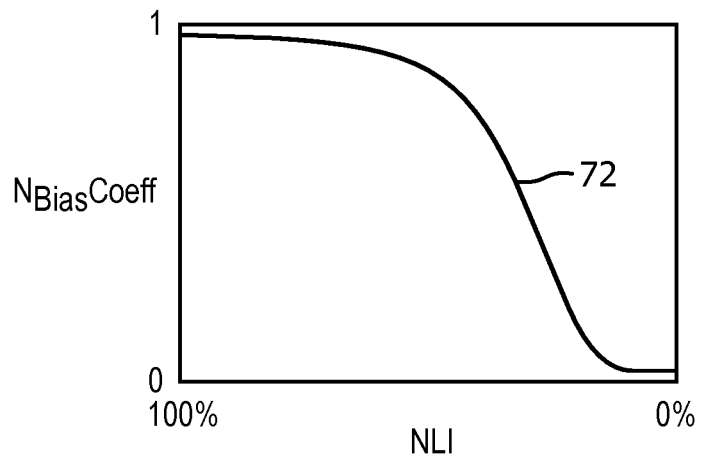
Figure 4B:
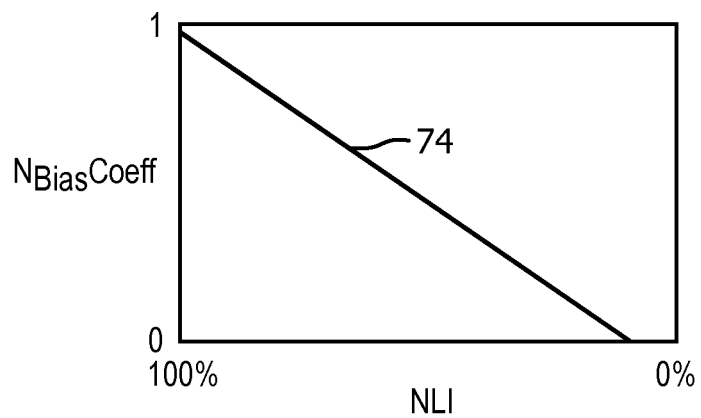
Figure 4C:
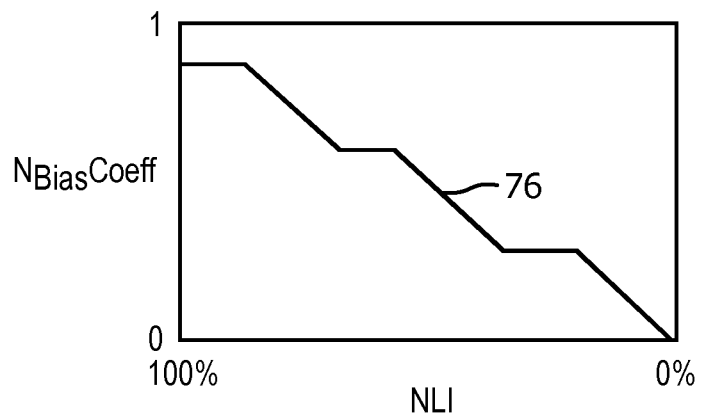

These noise likelihood estimations for the pixels are produced in the noise model module 32 and used to create noise bias coefficients ($N_{Bias}$Coeff) for use by the persistence processor to reduce image noise. The NLI values are converted to a range of values with a desired characteristic, examples of which are shown in FIG. 4. This is done, e.g., by using a mathematical formula or applying NLI values as inputs (addresses) to a lookup table containing output values exhibiting the desired characteristic. This lookup table is resident in $N_{Bias}$ processor 34 of the ultrasound system of FIG. 2. FIG. 4a illustrates a conversion characteristic which is a smooth curve 72. For high NLI values (strong likelihood of being noise), the $N_{Bias}$ processor produces high $N_{Bias}$Coeff values, which begin to decline around the middle of the NLI value range and approach zero for low NLI values. FIG. 4b shows an example where the relationship between the $N_{Bias}$Coeff values and the NLI values is entirely linear as seen by straight line 74. FIG. 4c gives an example where the $N_{Bias}$Coeff values decline in a stepwise fashion as the NLI values decline. Once the desired conversion characteristic is chosen, it can be implemented as a lookup table, where an input NLI value chooses a corresponding $N_{Bias}$Coeff value from the table. These or other conversion characteristics may be used in an implementation of the present invention.

The noise bias coefficients are applied to the persistence processor 30 where they are used to reduce image noise during persistence processing of ultrasound images. The persistence processor 30 in FIG. 2 also receives persistence coefficients (PersistCoeff) from a persistence controller 36 in response to the user setting a persistence control on the control panel 28. The user can turn persistence off, in which case there is no persistence processing. The user can turn persistence on to a low or high range of persistence settings, which will increase the persistence coefficients produced by the persistence controller and produce a greater degree of persistence. A single value of PersistCoeff produced by the persistence controller in response to a control setting can be used to process an entire image and can be used for each image processed. For instance, if there is little or no desired motion in the images, e.g., pulsatile blood flow, there is no desired motional effect to sustain by persistence and the user may decide to use low or no persistence. Alternatively, the lack of motion in the image means that there will be no image blurring when a high degree of persistence is employed, and a user may then decide to use a high persistence setting to increase the reduction of noise in the images without worrying about image blurring. Preferably, the persistence values for the processing of each pixel location vary both spatially and temporally. For instance, when the user is imaging the heart and trying to discern the peak blood flow velocity, a lower degree of persistence may be applied to color Doppler images acquired at and just following peak systole to avoid blurring the systolic peak, and a higher degree of persistence applied at other times and during diastole to achieve maximum noise reduction. At the same time, a lower degree of persistence may be used in B mode regions of the image where no flow is present, to reduce the possibility of blurring moving myocardial tissue. Other instances where persistence can be beneficially varied spatially or temporally will readily occur to those skilled in the art.

In accordance with the principles of the present invention, persistence processing is performed using both persistence control (PersistCoeff or, in short notation, Pc) and noise level control ($N_{Bias}$Coeff or, in short notation, Nb). Examples of persistence processors using both types of control are shown in FIGS. 5 and 6. FIG. 5 illustrates a persistence processor configured as an FIR filter. Pixels at a common location in a sequence of images I acquired at acquisition times $I_n$, $I_{n-1}$, $I_{n-2}$, and $1_{n-3}$ are applied to the filter inputs. The pixel values are weighted by persistence coefficients $Pc_0$, $Pc_1$, $Pc_t$, and $Pc_3$, respectively and are also weighted by noise bias coefficients $Nb_0$, $Nb_1$, $Nb_2$, and $Nb_3$. Thus, each pixel of each image is processed using both persistence coefficients and noise bias coefficients, which may vary temporally (across the filter inputs) and spatially (from one FIR filter for one pixel location to another FIR filter for another pixel location). The doubly weighted pixel values are summed at a summing node to produce an output pixel $O_n$ at the time of input image pixel $I_n$. While the noise bias weights are shown applied as product functions, they can alternatively be applied as summed values. Thus, an FIR filter implementation may take the form of $$O_n = \sum_{m=0}^{M-1} I_{n-m} Pc_m Nb_m$$

when the noise bias coefficient is applied as a product function, or the form of $$O_n = \sum_{m=0}^{M-1} I_{n-m} Pc_m - Nb_m$$

when the noise bias coefficient is applied as a summed value.

Figure 6A:
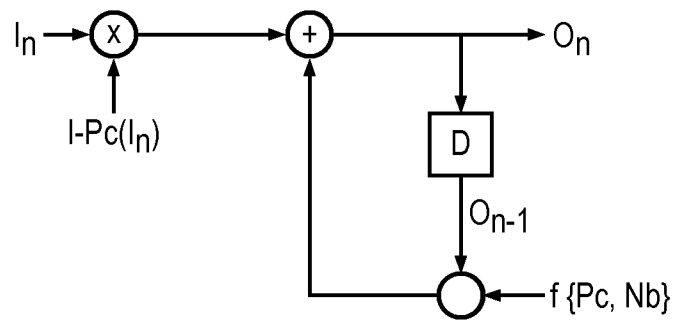

FIG. 6a illustrates a persistence processor of the present invention configured as an IIR filter. This example is a first order IIR filter, where a pixel of an input image $I_n$ is first multiplied by a weighting function $1-Pc(I_n)$. This weighted value is summed with a weighted delayed output value to produce the output value $O_n$. The previous output value is delayed by one processing interval (one frame interval) by a delay D to produce the previous output value $O_{n-1}$ for the current computation. The previous output value $O_{n-1}$ is weighted by f{Pc,Nb}, which is a value or expression which is a function of both a persistence coefficient (Pc) and a noise bias coefficient (Nb). That is, f{Pc,Nb} can be a product function, a summation function, or can combine the persistence and noise bias coefficients by some other mathematical operation. For example, a simple choice for f{Pc,Nb} could be Pc−Nb where Nn is the noise bias coefficient and Nb=0 corresponds to a default persistence algorithm which does not include a noise bias component.

The weighted previous output value is summed with the weighted input value at a summing node "+". Mathematically, this IIR filter executes the algorithm $$O_n = I_n(1-Pc(In)) + O_{n-1}(f\{Pc,Nb\})$$

The output of the persistence processor is coupled to a display processor 42 which suitably conditions the images for display on an image display 40.

Figure 6B:
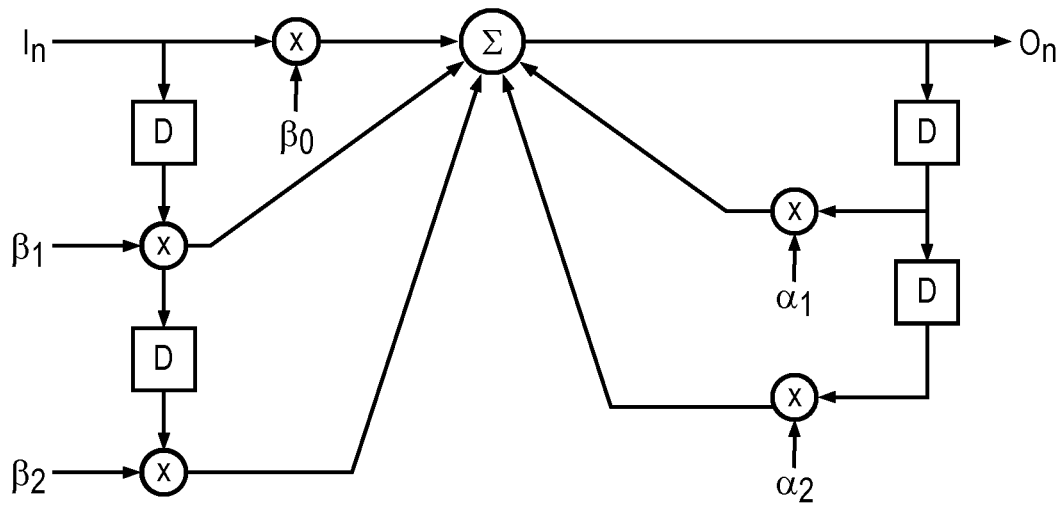

FIG. 6b illustrates a persistence processor of the present invention configured as a second order IIR filter. A pixel of an input image $I_n$ is weighted by a coefficient $\beta_0$ and applied to a summing node. The pixel of the previous input image at the same location in the image is has been delayed by a delay D (one image frame interval) and this $I_{n-1}$ pixel is weighted by a coefficient $\beta_1$ and applied to the summing node. The $I_{n-1}$ frame is delayed again by a delay D and this $I_{n-2}$ pixel is weighted by a coefficient $\beta_2$ and applied to the summing node. The output $O_n$ produced at the summing node was delayed by delay D to produce the previous output $O_{n-1}$ and by a second delay D to produce the output $O_{n-2}$ prior to that one. These previous outputs are weighted by coefficients $\alpha_1$ and $\alpha_2$ which are functions of the noise coefficients f{Pc, Nb}, and the two weighted previous outputs are applied to the summing node. The algorithm executed by this second order IIR filter is of the form $$O_n = I_n\beta_0 + I_{n-1}\beta_1 + I_{n-2}\beta_2 + O_{n-1}\alpha_1 + O_{n-2}\alpha_2$$

where $\beta_0$, $\beta_1$ and $\beta_2$ are functions of the persistence coefficient(s) and $\alpha_1$ and $\alpha_2$ are functions of both the persistent coefficient(s) and the noise bias coefficient(s).

In a constructed implementation, adjustment of a persistence control on the control panel 28 varies both the noise variance by control of PersistCoeff, and the noise floor by control of $N_{Bias}$Coeff. The persistence control can be implemented as a rotary knob, a slider switch, or a virtual control on a touchscreen. The PersistCoeff is variable between 0.0 and 1.0, with 0.0 implementing no persistence (persistence is turned off) and 1.0 being the most aggressive persistence. Increasing the PersistCoeff value increases the weighting applied to previous images, the number of images which are persisted, or both. The PersistCoeff values are also coupled to the $N_{Bias}$ processor 34, so as more aggressive persistence is selected, so is more aggressive noise floor processing. For example, when the user selects relatively low persistence with a PersistCoeff value of 0.3, the $N_{Bias}$ processor 34 may implement the linear conversion curve of FIG. 4b. But when the user dials up a stronger persistence with a PersistCoeff setting of 0.8, the $N_{Bias}$ processor switches to use of a more aggressive noise floor curve such as that of FIG. 4a, which produces more aggressive $N_{Bias}$Coeff values. Thus, as the user turns up the persistence and improves the noise variance characteristic of the images, the noise floor characteristic, the signal to noise ratio, is improved in tandem. In the constructed implementation, as the persistence control is turned up to increase persistence, noise in the images is seen to decrease and noisy image areas become noticeably darker and more noise-free. With less noise in the images, a user may decide to decrease persistence to reduce the possibility of image blurring due to motion, or may decide to increase the gain of the images to better visualize fine structure which might otherwise be obscured by noise. It will be appreciated that persistence control and noise floor control can alternatively be controlled by separate controls, rather than a single control as explained above.

An implementation of the present invention can be used to improve ultrasound images in all imaging modes, including B mode, color Doppler, color power, strain or shear wave elastography, and contrast imaging. It will be appreciated, that the noise bias control may not be used in color Doppler and other parametric imaging modes to change pixel values, as that would undesirably change the velocity or other parametric values indicated by the pixels. Instead, the noise bias control is used, in a color Doppler example, to control the color write priority, which determines whether a pixel is to be displayed as velocity or tissue or possibly a blend. For instance, color values near the noise floor may not be displayed as a result of noise processing, and tissue (B mode) pixel values displayed instead.

It should be noted that an ultrasound system suitable for use in an implementation of the present invention, and in particular the component structure of the ultrasound system of FIG. 2, may be implemented in hardware, software or a combination thereof. The various embodiments and/or components of an ultrasound system, for example, the noise model, the $N_{Bias}$ processor, the persistence controller, and the persistence processor, or components and controllers therein, also may be implemented as part of one or more computers or microprocessors. The computer or processor may include a computing device, an input device, a display unit and an interface, for example, for accessing the Internet. The computer or processor may include a microprocessor. The microprocessor may be connected to a communication bus, for example, to access a PACS system or the data network for importing training images. The computer or processor may also include a memory. The memory devices such as the image memory 26 and the memory device used to store the noise model 32 may include Random Access Memory (RAM) and Read Only Memory (ROM). The computer or processor further may include a storage device, which may be a hard disk drive or a removable storage drive such as a floppy disk drive, optical disk drive, solid-state thumb drive, and the like. The storage device may also be other similar means for loading computer programs or other instructions into the computer or processor.

As used herein, the term "computer" or "module" or "processor" or "workstation" may include any processor-based or microprocessor-based system including systems using microcontrollers, reduced instruction set computers (RISC), ASICs, logic circuits, and any other circuit or processor capable of executing the functions described herein. The above examples are exemplary only, and are thus not intended to limit in any way the definition and/or meaning of these terms.

The computer or processor executes a set of instructions that are stored in one or more storage elements, in order to process input data. The storage elements may also store data or other information as desired or needed. The storage element may be in the form of an information source or a physical memory element within a processing machine.

The set of instructions of an ultrasound system including those controlling the acquisition, processing, and transmission of ultrasound images as described above may include various commands that instruct a computer or processor as a processing machine to perform specific operations such as the methods and processes of the various embodiments of the invention. The set of instructions may be in the form of a software program. The software may be in various forms such as system software or application software and which may be embodied as a tangible and non-transitory computer readable medium. Further, the software may be in the form of a collection of separate programs or modules, a program module within a larger program or a portion of a program module. One skilled in the art will recognize, for instance, that the persistence processor is most likely best implemented as a software module. The software also may include modular programming in the form of object-oriented programming. The processing of input data by the processing machine may be in response to operator commands, or in response to results of previous processing, or in response to a request made by another processing machine.

Furthermore, the limitations of the following claims are not written in means-plus-function format and are not intended to be interpreted based on 35 U.S.C. 112, sixth paragraph, unless and until such claim limitations expressly use the phrase "means for" followed by a statement of function devoid of further structure.

What is claimed is:

1. An ultrasound imaging system for producing images with improved noise performance, comprising:
    an ultrasound probe adapted to acquire ultrasound echo signals from an image field for imaging;
    an image processor that is coupled to the probe and adapted to produce an ultrasound image;
    a memory comprising a noise model representing noise levels of pixel locations of the ultrasound image, wherein the noise model is further adapted for comparison with pixel values of an image to determine a likelihood that a pixel value is noise;
    a noise bias coefficient processor that is adapted to produce noise bias coefficients by:
        comparing the pixel values of the ultrasound image with the noise model to determine the likelihood that a pixel is noise; and
        producing noise bias coefficients that are a function of the likelihood that a pixel value is noise;
    a persistence processor which, based on persistence control coefficients and the noise bias coefficients, is adapted to improve noise performance of ultrasound images; and
    a persistence control adapted for operation by a user to select persistence control coefficients for a low range or a high range of persistence settings, wherein increasing a persistence control coefficient increases a weighting applied to previous images, the number of images which are persisted, or both, for more aggressive persistence,
    wherein the selected persistence control coefficients are further coupled to the noise bias coefficient processor so that as more aggressive persistence is selected, more aggressive noise processing is implemented to improve the signal to noise ratio of the ultrasound image.

2. The ultrasound imaging system of claim 1, wherein the noise model is at least partially based on receive amplifier noise of the ultrasound system, or from correlation among pixel values in the ultrasound images.

3. The ultrasound imaging system of claim 1, wherein the noise model is at least partially based on ultrasound image data acquired in an absence of ultrasound signal transmission, or from ultrasound image data of a noise spectrum.

4. The ultrasound imaging system of claim 1, wherein the noise bias coefficient processor is further adapted to produce noise bias coefficients over a range that exhibits a desired conversion characteristic between the likelihood that a pixel value is noise and the noise bias coefficient.

5. The ultrasound imaging system of claim 4, wherein the desired conversion characteristic further comprises a curve.

6. The ultrasound imaging system of claim 1, wherein the persistence processor further comprises one of a finite impulse response filter or an infinite impulse response filter.

7. A method for producing images with improved noise performance, comprising:
    acquiring ultrasound echo signals from an image field for imaging;
    producing an ultrasound image from the ultrasound echo signals;
    obtaining a noise level model of pixels of an ultrasound image, wherein the noise level model is adapted for comparison with pixel values of an image to determine a likelihood that a pixel value is noise;
    producing noise bias coefficients by:
        comparing the pixel values of the ultrasound image with the noise model to determine the likelihood that a pixel is noise; and
        producing noise bias coefficients that are a function of the likelihood that a pixel value is noise;
    adjusting a user-operable persistence control to produce a persistence coefficient for a greater degree of persistence by increasing a weighting applied to previous images, the number of images which are persisted, or both, for more aggressive persistence;
    persistence processing ultrasound images in response to both the noise bias coefficients and persistence coefficients to improve the noise performance of images processed with persistence,
    wherein the production of a greater degree of persistence also produces more aggressive noise processing to improve the signal to noise ratio of the ultrasound image.

8. The method of claim 7, wherein obtaining the noise level model comprises using system amplifier noise properties, performing frame to frame image correlation, receiving an image in the absence of transmission, receiving an image from a noise spectrum, or a combination thereof.

9. The method of claim 7, wherein persistence processing comprises processing images with a finite impulse response filter or an infinite impulse response filter operating in response to both the noise bias values and the user persistence control input.

* * * * *